(12) United States Patent
Mine et al.

(10) Patent No.: US 11,256,898 B2
(45) Date of Patent: Feb. 22, 2022

(54) CULTURE INFORMATION PROCESSING DEVICE

(71) Applicant: OLYMPUS CORPORATION, Tokyo (JP)

(72) Inventors: Taiji Mine, Tokyo (JP); Yasunobu Iga, Tokyo (JP); Yoshinobu Akahori, Tokyo (JP); Koji Sakai, Tokyo (JP); Kazunari Tokuda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 140 days.

(21) Appl. No.: 16/835,704

(22) Filed: Mar. 31, 2020

(65) Prior Publication Data
US 2020/0234032 A1    Jul. 23, 2020

Related U.S. Application Data

(63) Continuation of application No. PCT/JP2017/036018, filed on Oct. 3, 2017.

(51) Int. Cl.
*G06K 9/00* (2006.01)
*C12M 1/34* (2006.01)
*G06T 7/00* (2017.01)

(52) U.S. Cl.
CPC ....... *G06K 9/00127* (2013.01); *C12M 1/3446* (2013.01); *C12M 41/36* (2013.01);
(Continued)

(58) Field of Classification Search
CPC ........... G06K 9/00127; G06K 2209/05; C12M 1/3446; C12M 41/36; C12M 41/48;
(Continued)

(56) References Cited

U.S. PATENT DOCUMENTS

2015/0259640 A1   9/2015   Kimura
2015/0353884 A1   12/2015  Ozaki et al.
(Continued)

FOREIGN PATENT DOCUMENTS

EP   2918671 A1    9/2015
EP   2 949 746 A1  12/2015
(Continued)

OTHER PUBLICATIONS

International Search Report dated Jan. 9, 2018 issued in PCT/JP2017/036018.
(Continued)

*Primary Examiner* — Atiba O Fitzpatrick
(74) *Attorney, Agent, or Firm* — Scully, Scott, Murphy & Presser, P.C.

(57) ABSTRACT

A culture information processing device includes: a feature value computing unit that computes growth feature values indicating features of growth characteristics of cells from data acquired in a particular first subculturing process selected from among a plurality of subculturing processes included in a culture period of the cells; a condition setting unit that sets culturing conditions of a second subculturing process one process after the first subculturing process; and an information computing unit that computes, on the basis of the growth feature values computed by the feature value computing unit and the culturing conditions set by the condition setting unit, characteristics-related information related to growth characteristics in the second subculturing process.

11 Claims, 7 Drawing Sheets

(52) U.S. Cl.
CPC ........ *G06T 7/0016* (2013.01); *G06K 2209/05* (2013.01); *G06T 2207/10056* (2013.01); *G06T 2207/30024* (2013.01)

(58) Field of Classification Search
CPC ......... G06T 7/0016; G06T 2207/10056; G06T 2207/30024; G06T 7/0012; G06T 2207/30101; G06T 2207/10061; G06T 2207/30242; G02B 21/365
See application file for complete search history.

(56) References Cited

U.S. PATENT DOCUMENTS

| | | | |
|---|---|---|---|
| 2016/0258968 | A1 | 9/2016 | Jain et al. |
| 2017/0059558 | A1 | 3/2017 | Eisele et al. |
| 2017/0100714 | A1 | 4/2017 | Jain et al. |
| 2017/0177789 | A1 | 6/2017 | Iga et al. |
| 2017/0204359 | A1 | 7/2017 | Ando et al. |
| 2018/0112173 | A1* | 4/2018 | Wiles .................... G06T 7/0016 |
| 2018/0185839 | A1 | 7/2018 | Jain et al. |
| 2019/0049426 | A1* | 2/2019 | Lee ......................... G01N 15/14 |
| 2019/0078047 | A1* | 3/2019 | Ando .................... G02B 21/367 |
| 2019/0078048 | A1 | 3/2019 | Ando et al. |

FOREIGN PATENT DOCUMENTS

| | | |
|---|---|---|
| EP | 3171158 A1 | 5/2017 |
| JP | 2001-224366 A | 8/2001 |
| JP | 2005-224106 A | 8/2005 |
| JP | 2007-124914 A | 5/2007 |
| JP | 2010-152829 A | 7/2010 |
| JP | 2015-171344 A | 10/2015 |
| JP | 2016-023942 A | 2/2016 |
| JP | 2016-534714 A | 11/2016 |
| JP | 2017-506892 A | 3/2017 |
| WO | 2014/115799 A1 | 7/2014 |
| WO | WO 2015/102726 A2 | 7/2015 |
| WO | WO 2015/124618 A1 | 8/2015 |
| WO | WO 2016/098271 A1 | 6/2016 |

OTHER PUBLICATIONS

Japanese Office Action dated Apr. 6, 2021 received in 2019-546447.
Japanese Office Action dated Nov. 30, 2021 received in 2019-546447.

* cited by examiner

CULTURE INFORMATION PROCESSING DEVICE

CROSS-REFERENCE TO RELATED APPLICATIONS

This is a continuation of International Application PCT/JP2017/036018 which is hereby incorporated by reference herein in its entirety.

TECHNICAL FIELD

The present invention relates to a culture information processing device.

BACKGROUND ART

There is a known method of culturing cells, such as iPS cells, by subculturing and monitoring the culturing characteristics (for example, see PTL 1).

Also known is to quantify the features of the acquired data into parameters of a model formula by fitting the model formula to the acquired data (for example, see PTL 2).

CITATION LIST

Patent Literature

{PTL 1}
Japanese Unexamined Patent Application, Publication No. 2015-171344
{PTL 2}
Japanese Translation of PCT International Application, Publication No. 2016-534714

SUMMARY OF INVENTION

An aspect of the present invention provides a culture information processing device including: a feature value computing unit that computes growth feature values indicating the features of growth characteristics of cells from data acquired in a particular first subculturing process selected from among a plurality of subculturing processes included in a culture period of the cells; a condition setting unit that sets culturing conditions of a second subculturing process one process after the first subculturing process; and an information computing unit that computes, on the basis of the growth feature values computed by the feature value computing unit and the culturing conditions set by the condition setting unit, characteristics-related information related to growth characteristics in the second subculturing process.

Another aspect of the present invention provides a culture information processing device including: an input device through which data acquired in a first subculturing process selected from among a plurality of subculturing processes included in subculturing of cells and culturing conditions of a second subculturing process one process after the first subculturing process are input; a storage that stores the data and the culturing conditions input through the input device; and a processor that computes, on the basis of the data and the culturing conditions stored in the storage, characteristics-related information related to growth characteristics of the second subculturing process. The processor computes growth feature values indicating the features of growth characteristics of the cells in the first subculturing process from the data stored in the storage, and computes the characteristics-related information on the basis of the computed growth feature values and the culturing conditions stored in the storage.

Yet another aspect of the present invention provides a culture information processing device including: a storage that stores data acquired in a first subculturing process selected from among a plurality of subculturing processes included in subculturing of cells and culturing conditions of a second subculturing process one process after the first subculturing process; and a processor that computes, on the basis of the data and the culturing conditions stored in the storage, characteristics-related information related to growth characteristics of the second subculturing process. The processor computes growth feature values indicating the features of growth characteristics of the cells in the first subculturing process from the data stored in the storage, and computes the characteristics-related information on the basis of the computed growth feature values and the culturing conditions stored in the storage.

Still another aspect of the present invention provides a culture information processing device, in which growth feature values that indicate features of growth characteristics of cells in a first subculturing process selected from among a plurality of subculturing processes included in subculturing of the cells and that are computed on the basis of data acquired in the first subculturing process, and culturing conditions of a second subculturing process one process after the first subculturing process are input, and, on the basis of the input growth feature values and culturing conditions, characteristics-related information related to growth characteristics of the second subculturing process is computed.

DESCRIPTION OF EMBODIMENTS

A culture information processing device 1 according to one embodiment of the present invention will now be described with reference to the drawings.

Figure 1:
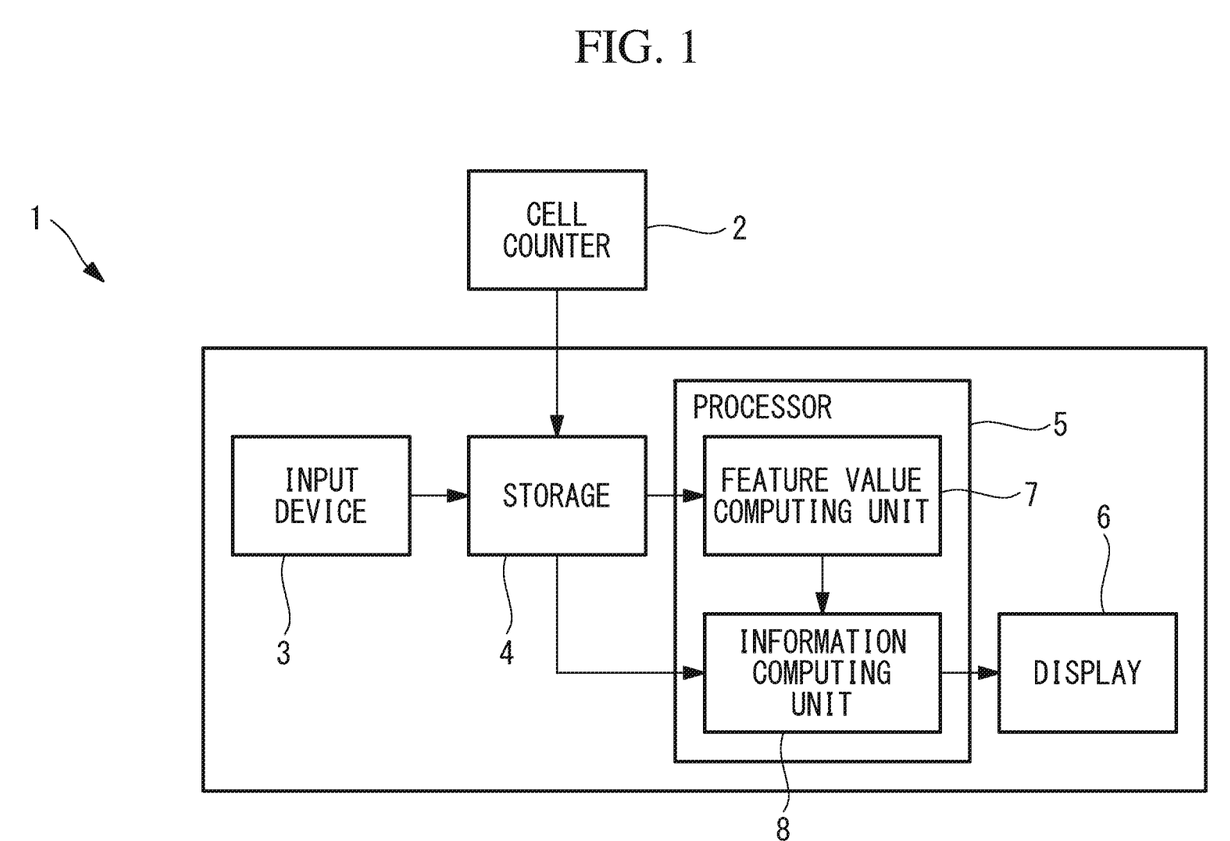
FIG. 1 is an overall view illustrating a culture information processing device according to one embodiment of the present invention.

As illustrated in FIG. 1, the culture information processing device 1 of this embodiment is a computer connected to a cell counter (input device) 2 that measures cell information such as the cell count and the cell density of the cells being cultured. The culture information processing device 1 is equipped with: an input device (condition setting unit) 3, such as a mouse or a keyboard, for inputting culturing conditions; a storage 4 that stores the cell information measured by the cell counter 2 and the culturing conditions input through the input device 3; a processor 5 that computes growth characteristics on the basis of the cell information and the culturing conditions stored in the storage 4; and a display 6.

The cell counter 2 has, mounted therein, a culture vessel that contains a medium seeded with cells, and chronologically obtains images of growing cells attached to the bottom surface of the culture vessel.

Figure 2:
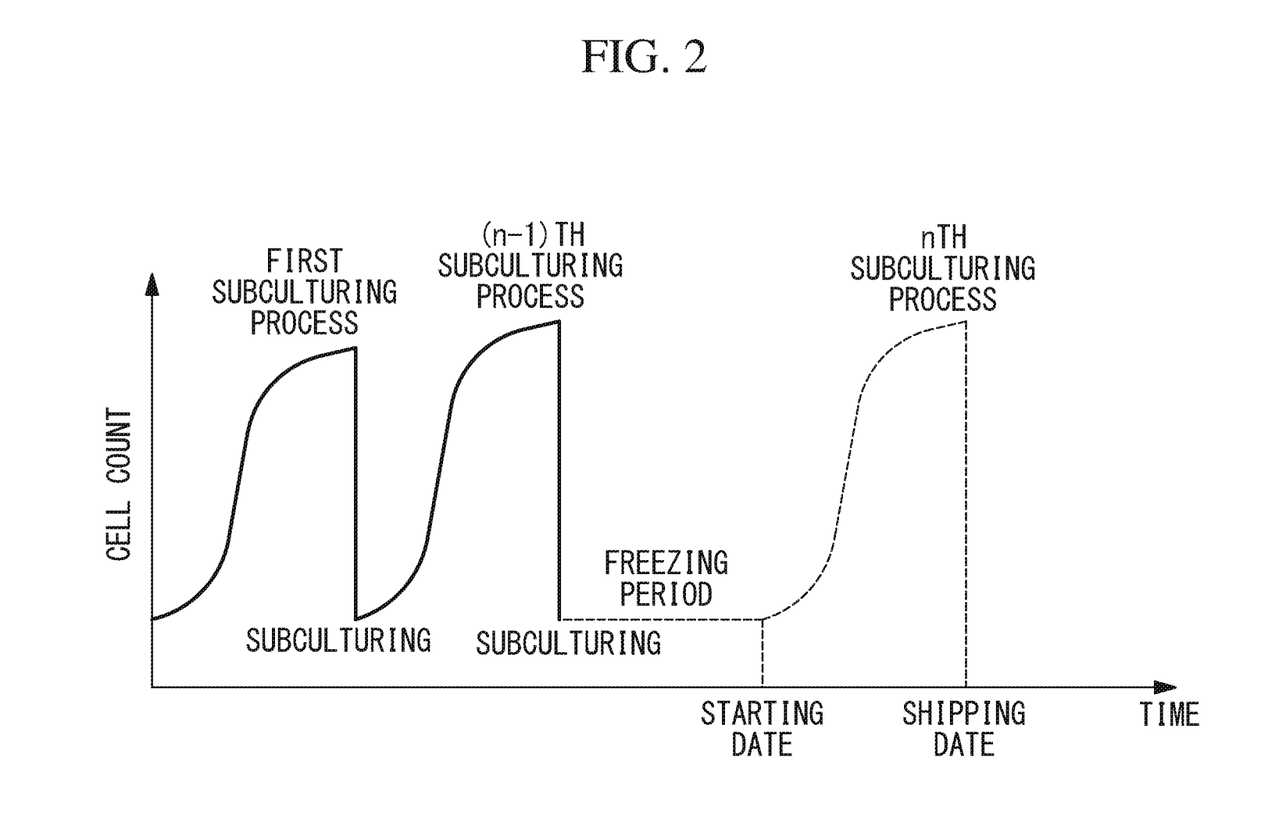
FIG. 2 is a graph indicating one example of changes in cell count over time in one culture vessel used in a subculture to which the culture information processing device illustrated in FIG. 1 is applied.

As illustrated in FIG. 2, the cell culturing includes multiple subculturing processes resulting from performing subculturing multiple times. In other words, when the culture is started and cells are grown to confluence, a subculture operation of temporarily detaching the cells from the culture vessel and re-distributing the detached cells to more than one culture vessels is performed. Thus, as illustrated in FIG. 2, the cell count gradually increases from the initial value in each subculturing process, and is reset to the initial value as the cells are seeded in a new culture vessel by subculturing.

The culturing conditions, such as the type and concentration of the medium, are input through the input device 3. In the cell culturing, the required amount of cells (required number of cells) must be cultured by the required shipping time (shipping date: the end date of the nth subculturing process); thus, such information is also input through the input device 3.

The storage 4 is any storage device such as a memory device or a hard disk device, and sequentially stores the images from the cell counter 2 in association with the time at which the images are acquired. The culturing conditions input through the input device 3 are also stored in the storage 4. The information such as the shipping time and the required number of cells also constitute the culturing conditions, and are input through the input device 3 and stored in the storage 4.

The processor 5 is equipped with a feature value computing unit 7 that processes the images stored in the storage 4 so as to obtain the cell count and generate chronologically ordered data, and fits the formula for a growth curve to the data so as to compute feature values indicating the features of the growth characteristics. One example of the growth curve is a logistic curve expressed by the formula below, and examples of the feature values indicating the features of the growth characteristics are the following coefficients $N_0$, $K$, and $r$ expressing the logistic curve.

$$N=K/(1+(K/N_0-1)e^{-rt})$$

Here, N represents the cell count, $N_0$ represents the initial cell count, K represents the carrying capacity, r represents the growth rate, and t represents time.

The computed feature values are stored in the storage 4 in association with the subculturing process numbers.

In addition, the processor 5 is equipped with an information computing unit 8 that, on the basis of the feature values in a particular subculturing process (first subculturing process), computed by the feature value computing unit 7 and stored in the storage 4, and the culturing conditions input through the input device 3 so as to serve as the culturing conditions of a subculturing process (second subculturing process) one after the aforementioned particular subculturing process, computes characteristics-related information related to the growth characteristics in the second subculturing process.

Examples of the characteristics-related information eventually output from the information computing unit 8 include the graph indicating the growth characteristics, and the feature values indicating the features of the growth characteristics.

That is, according to the culture information processing device 1 of this embodiment, based on the feature values indicating the features of the growth characteristics obtained in any first subculturing process selected from among the repeated subculturing processes, and the culturing conditions of the next, second subculturing process, the graph indicating the growth characteristics in the second subculturing process or the feature values thereof are output as the characteristics-related information. Thus, since the characteristics-related information is acquired, it becomes possible to determine when the starting date of the second subculturing process should be in order to obtain the required number of cells on the shipping date input as part of the culturing conditions.

In this case, a freezing period for freezing the cells is preferably set between the (n−1)th subculturing process (first subculturing process) and the last nth subculturing process (second subculturing process) in the entire culture period that includes n subculturing processes.

In this manner, the starting time for the nth subculturing process for obtaining the input required number of cells at the input shipping time can be easily set by adjusting the length of the freezing period.

The operation of the thus-configured culture information processing device 1 according to this embodiment will now be described.

Figure 3:
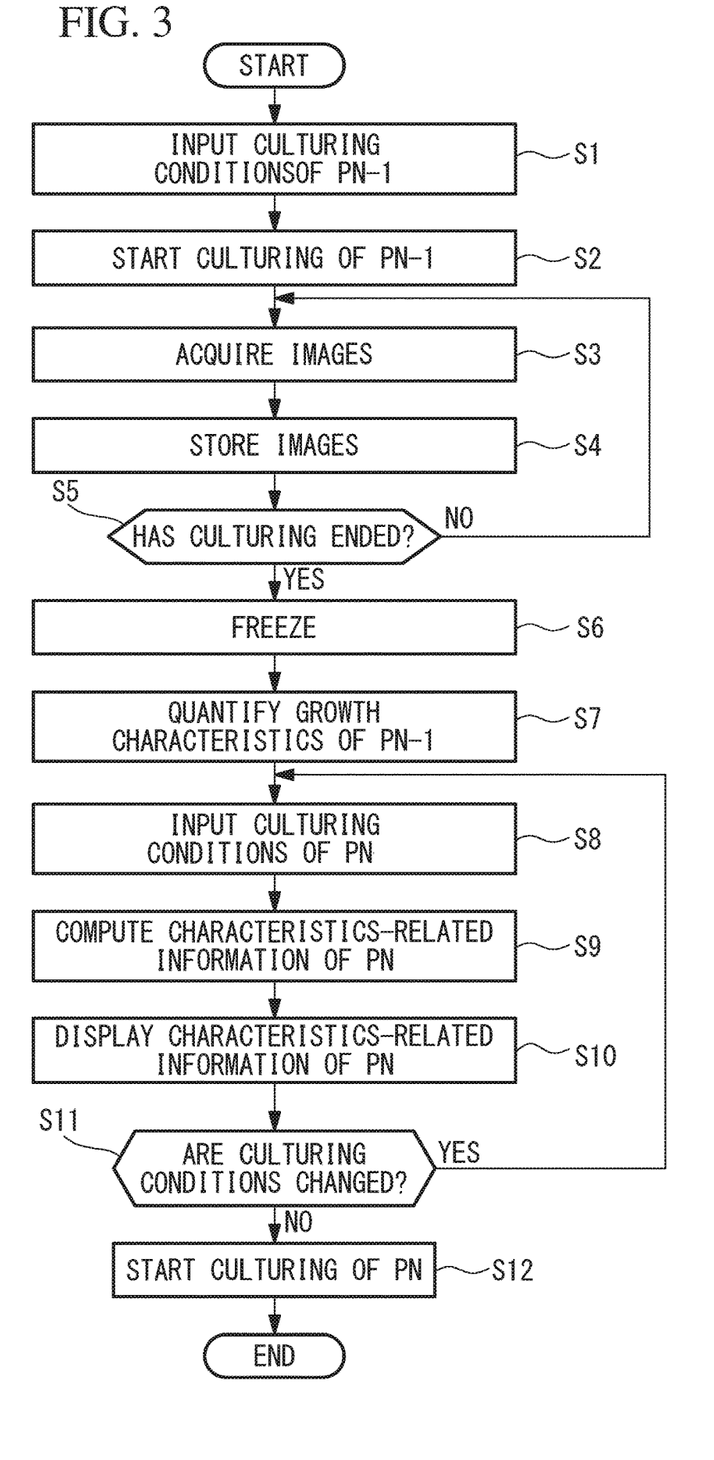
FIG. 3 is a flowchart illustrating the culture procedure performed with the culture information processing device illustrated in FIG. 1.

As illustrated in FIG. 3, in order to predict the growth characteristics of an nth subculturing process PN by using the culture information processing device 1 of this embodiment, culturing conditions of the (n−1)th subculturing process (first subculturing process) PN−1 are input through the input device 3 (step S1), and cell culturing of the (n−1)th subculturing process PN−1 is started (step S2). In this subculturing process PN−1, images of cells are acquired over time by the cell counter 2 (step S3), and are input to the culture information processing device 1 and stored in the storage 4 (step S4).

The ending time of the subculturing process PN−1 is judged on the basis of whether the cells inside the culture vessel have reached confluency (step S5). If NO, the steps from step S3 are repeated. If YES, the cells are detached from the culture vessel and frozen (step S6).

The images acquired from the start to the end of the subculturing process PN−1 are processed in the feature value computing unit 7 of the processor 5 so as to generate data indicating the growth characteristics, in which the cell counts extracted from the respective images are aligned in chronological order. The growth curve is fitted to the data to quantify the growth characteristics (step S7), and the quantified growth characteristics are stored in the storage 4.

Next, the culturing conditions of the nth subculturing process PN are input through the input device 3 (step S8), and the input culturing conditions are stored in the storage 4.

Based on the feature values indicating the growth characteristics of the (n−1)th subculturing process PN−1 and the culturing conditions of the n-th subculturing process PN stored in the storage 4, the characteristics-related information related to the growth characteristics in the subculturing process PN is computed by the information computing unit 8 (step S9), and displayed on the display 6 (step S10). The output method involves displaying, on the display 6, a graph indicating the growth characteristics of the subculturing process PN to be performed next or the feature values indicating the growth characteristics.

Since the characteristics-related information related to the growth characteristics of the subculturing process PN is displayed, the user can estimate the length of time needed to obtain the required number of cells from the start of the subculturing process PN. Thus, when to start the subculturing process PN in order to obtain the required number of cells in the subculturing process PN by the shipping time can be determined, and the length of the freezing period is adjusted to thaw the cells and to initiate the subculturing process PN at the determined starting time (step S12). In this manner, the required number of cells can be obtained by the shipping time.

If an effective starting time for the subculturing process PN cannot be obtained, for example, if the length of the time needed to obtain the required number of cells from the start of the subculturing process PN as estimated from the displayed characteristics-related information is so long that the freezing period cannot be secured, the steps from step S8 are repeated so that the user is urged to input new culturing conditions that shorten the time needed to obtain the required number of cells from the start of the subculturing process PN (step S11).

Figure 4:
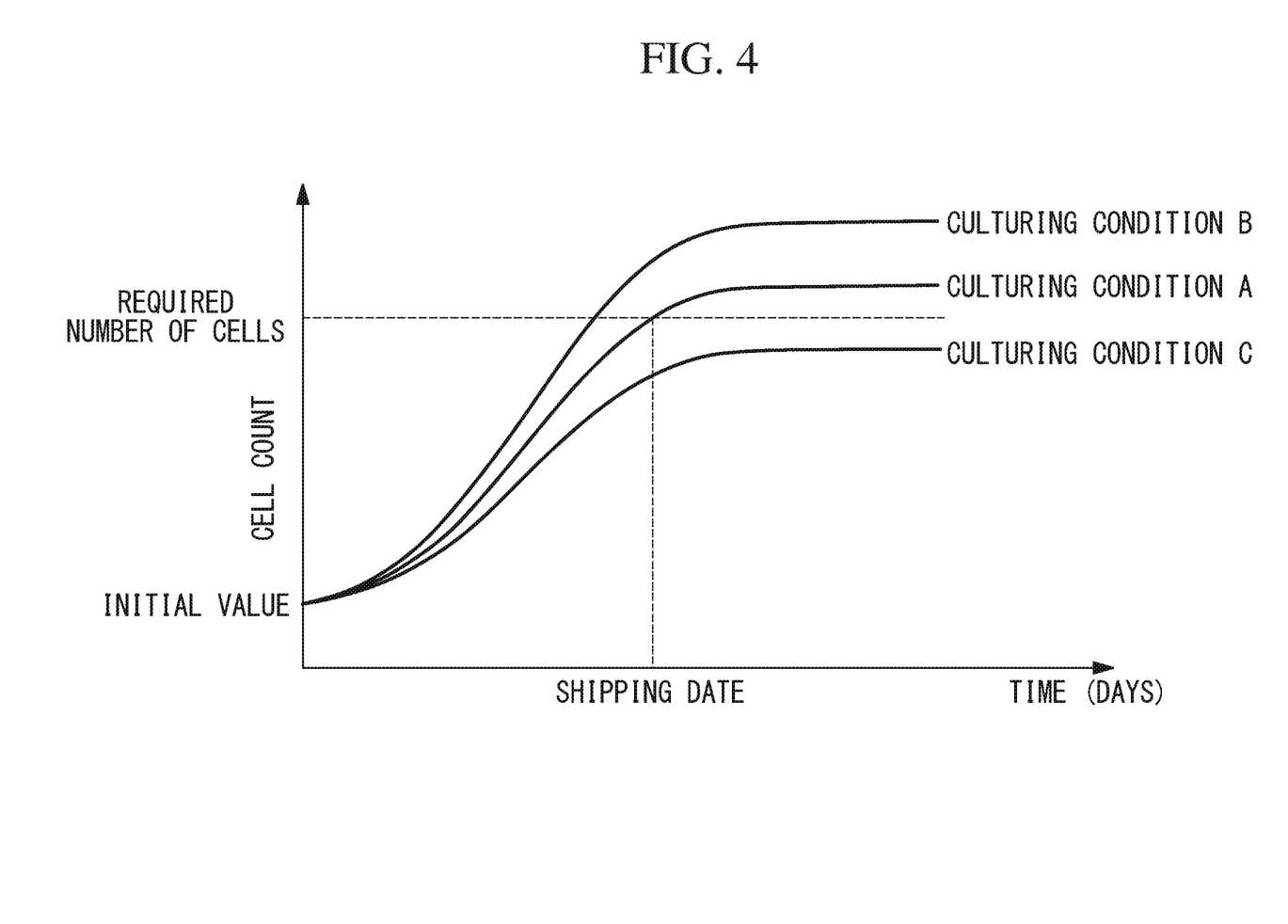
FIG. 4 is a graph indicating one example of changes in cell growth characteristics in the respective subculturing processes depending on the culturing conditions.

FIG. 4 is a graph indicating growth characteristics. The graph shows that varying the culturing conditions A, B, and C can change the number of days needed to obtain the required number of cells.

Here, in the subculturing processes PN−1 and PN, the growth characteristics of the cells greatly differ for each subculture; however, the inventors have found that the growth characteristics of the nth subculturing process PN are relatively strongly correlated with the growth characteristics of the (n−1)th subculturing process PN−1. A specific correlation between two adjacent subculturing processes PN−1 and PN can be estimated, for example, from the correlation between the growth characteristics of two adjacent subculturing processes obtained among the first to (n−1)th subculturing processes during the culture period. Alternatively, the correlation may be estimated from the correlation between the growth characteristics of two adjacent subculturing processes in culturing performed at a different time from the aforementioned culture period but with similar cells under similar culturing conditions.

Furthermore, the culturing conditions in the second subculturing process PN can be set to be the same as the culturing conditions in the first subculturing process PN−1 input through the input device 3 in step S1. In this manner, the task of setting the culturing conditions for each of the subculturing processes PN−1 and PN in step S8 can be eliminated.

Figure 5:
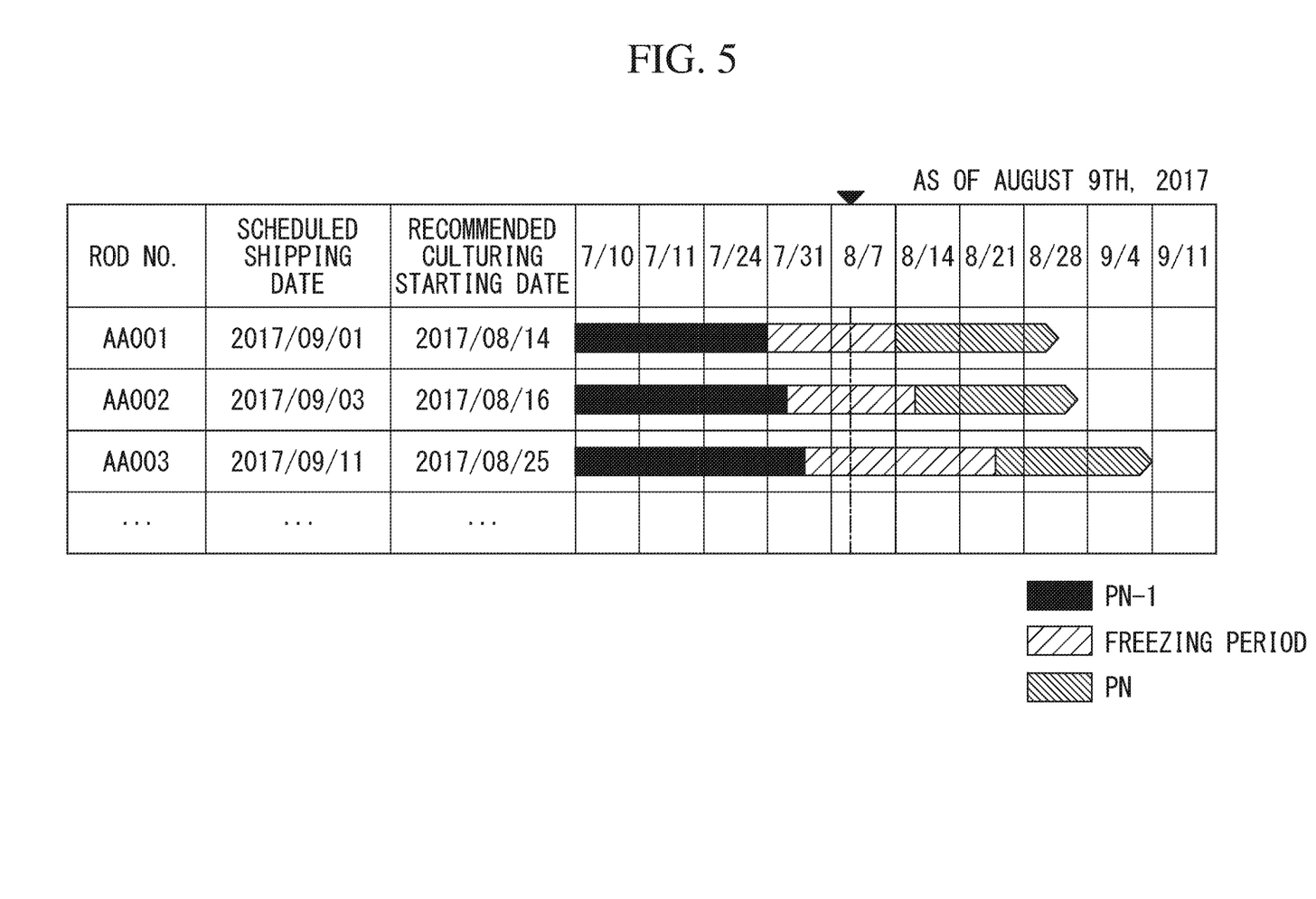
FIG. 5 is a chart indicating an example of the output of culture-related information according to a modification of the culture information processing device illustrated in FIG. 1.

Note that, in the culture information processing device 1 of this embodiment, the graph indicating the growth characteristics or the feature values indicating the features of the growth characteristics are displayed as the characteristics-related information; alternatively, as illustrated in FIG. 5, a recommended culturing starting date, which is the starting time for the nth subculturing process PN for obtaining the required number of cells on the scheduled shipping date may be displayed. In the example illustrated in FIG. 5, subcultures of more than one type of cells are simultaneously in progress. The culturing conditions, including the scheduled shipping dates for the respective subcultures, are input, and, as a result, the recommended culturing starting date on which the n-th subculturing process PN is to be started and the timing charts are displayed.

Alternatively, the scheduled shipping date and the starting time of the nth subculturing process PN may be input as the culturing conditions so as to estimate and display other culturing conditions.

Moreover, instead of displaying the starting time of the nth subculturing process PN estimated under particular culturing conditions, various starting times for the nth subculturing process PN under different culturing conditions may be displayed. Alternatively, various culturing conditions derived by varying the starting time of the nth subculturing process PN may be displayed.

Although a computer directly connected to the cell counter 2 is described as an example of the culture information processing device 1 in this embodiment, the culture information processing device 1 may be completely housed in the cell counter 2.

Figure 6:
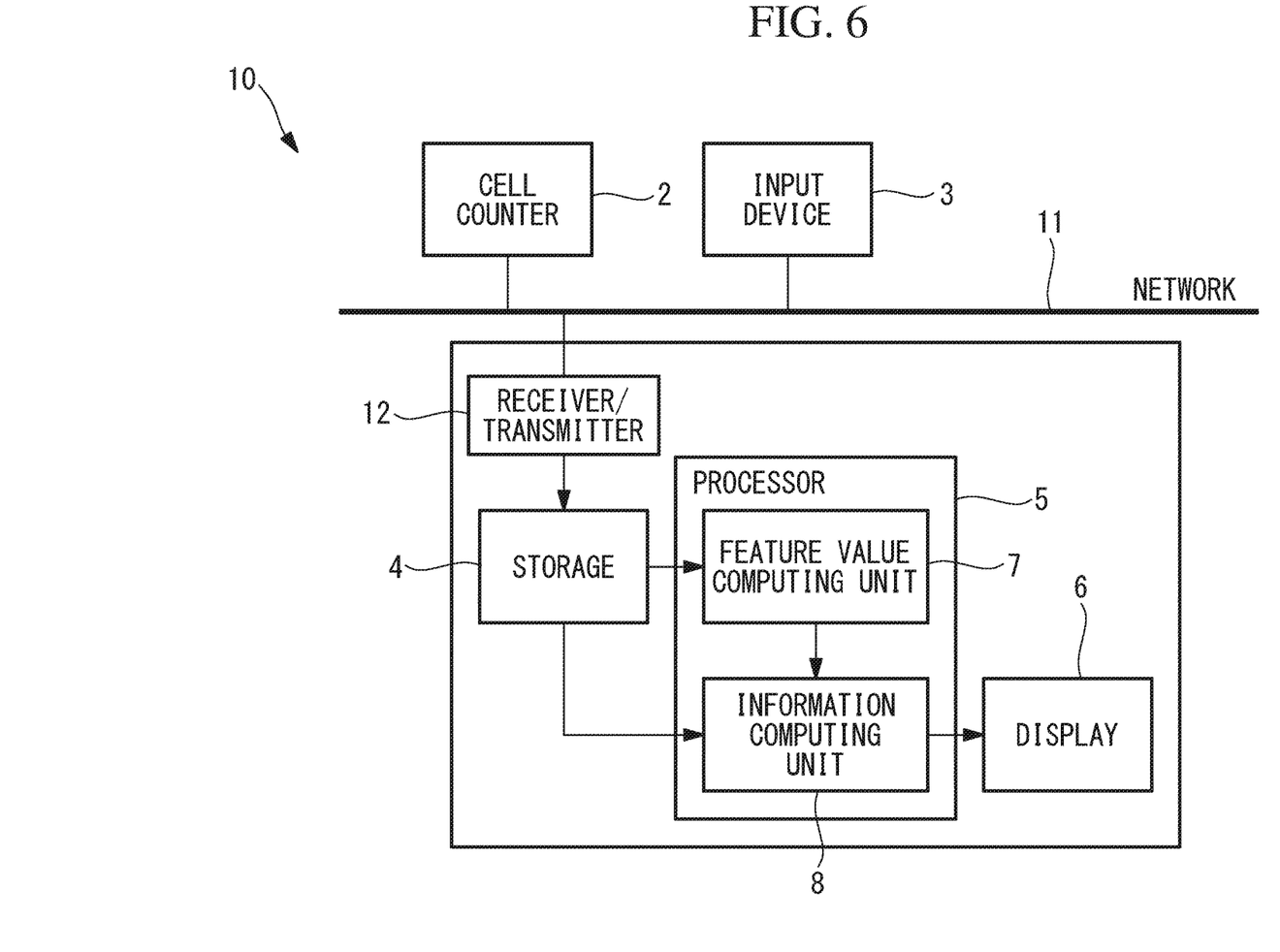
FIG. 6 is an overall diagram illustrating a modification of the culture information processing device illustrated in FIG. 1.

Furthermore, as illustrated in FIG. 6, a culture information processing device 10 equipped with a transmitter/receiver 12 that receives, via a network 11, images and culturing conditions from the cell counter 2 and the input device 3 connected via the network 11 may be provided.

Although the feature value computing unit 7 determines the cell count by processing the images received from the cell counter 2 in the embodiment described above, the images may be processed and the cell count may be determined by the cell counter 2, and the culture information processing device 1 may receive the cell count from the cell counter 2.

Figure 7:
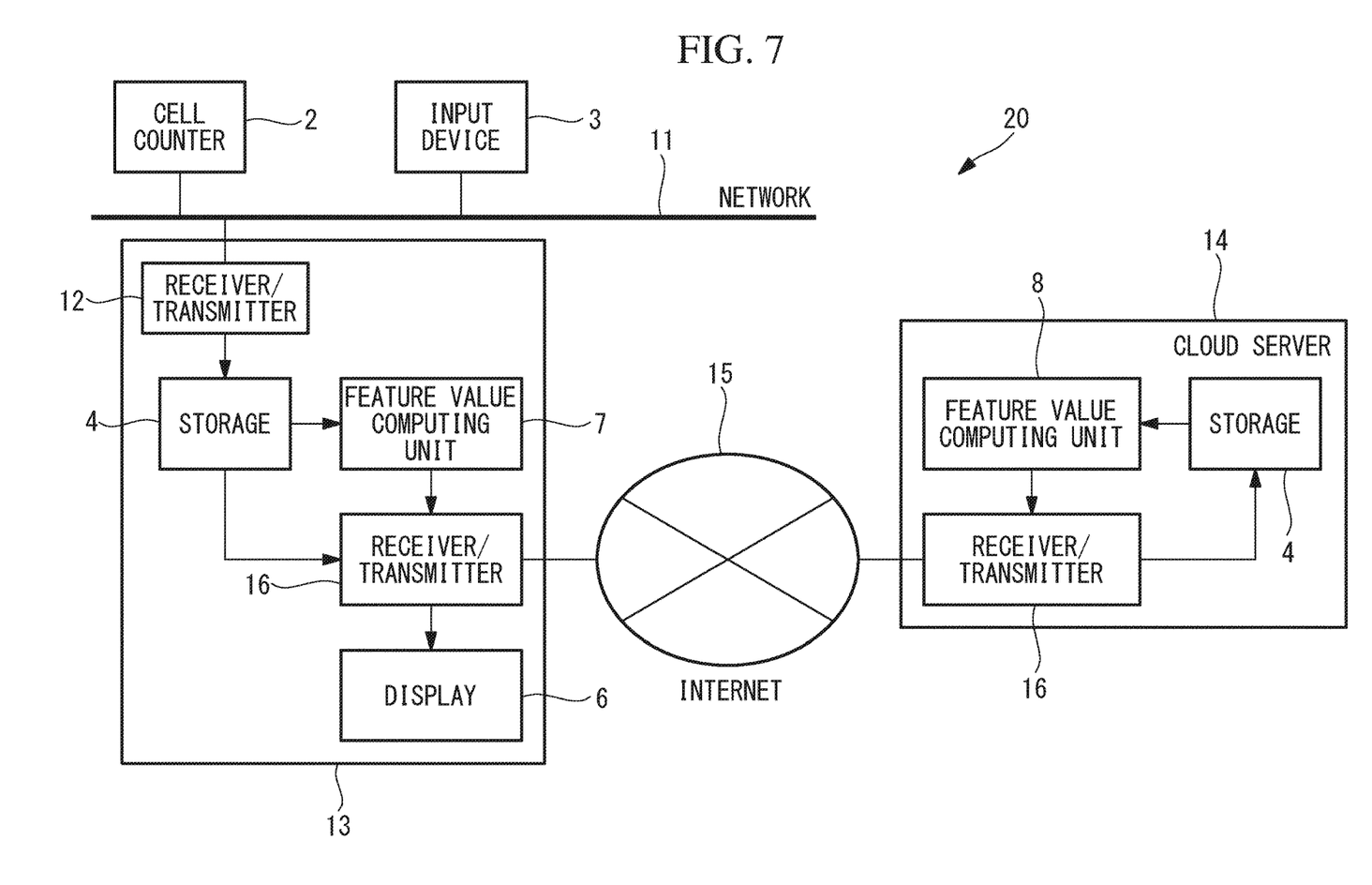
FIG. 7 is an overall diagram illustrating another modification of the culture information processing device illustrated in FIG. 1.

Alternatively, as illustrated in FIG. 7, a system 20 that includes a terminal 13 that receives images etc., from the cell counter 2, quantifies the growth characteristics in the (n−1)th subculturing process PN−1, and displays the characteristics-related information of the nth subculturing process PN, and a cloud server (culture information processing device) 14 that computes the characteristics-related information of the nth subculturing process PN from the input culturing conditions and the quantified growth characteristics of the (n−1)th subculturing process PN−1 may be provided. The terminal 13 and the cloud server 14 are connected through the internet 15. In this case, each of the terminal 13 and the cloud server 14 is equipped with a receiver/transmitter 16 that transmits and receives the growth characteristics, the culturing conditions, the characteristics-related information, etc., via the internet 15.

The above-described embodiment leads to the following aspects.

An aspect of the present invention provides a culture information processing device including: a feature value computing unit that computes growth feature values indicating the features of growth characteristics of cells from data acquired in a particular first subculturing process selected from among a plurality of subculturing processes included in a culture period of the cells; a condition setting unit that sets culturing conditions of a second subculturing process one process after the first subculturing process; and an information computing unit that computes, on the basis of the growth feature values computed by the feature value computing unit and the culturing conditions set by the condition setting unit, characteristics-related information related to growth characteristics in the second subculturing process.

According to this aspect, the feature value computing unit computes the growth feature values indicating the features of the growth characteristics of the cells from the data acquired in the first subculturing process, and the culturing conditions of the second subculturing process one process after the first subculturing process are set by the condition setting unit.

The inventors have found that there is a relatively strong correlation between the growth characteristics of the cells in the adjacent two subculturing processes. In addition, the growth characteristics of the cells are known to vary depending on the type and concentration of the media, etc.

Thus, when the growth feature values computed by the feature value computing unit from the data acquired in the first subculturing process one process before the second subculturing process and the culturing conditions in the second subculturing process set by the condition setting unit are used as the basis of the computation, the characteristics-related information related to the growth characteristics of the cells in the second subculturing process can be accurately computed prior to performing the second subculturing process. In this manner, the ending time for obtaining the target cell yield by subculturing, the starting time of the second subculturing process, and other culturing conditions can be estimated, and a culture schedule can be established.

In the aspect described above, the condition setting unit may set culturing conditions of the first subculturing process, and set, for the second subculturing process, culturing conditions other than when to culture to be identical to the culturing conditions of the first subculturing process.

In this manner, cells can be cultured in the second subculturing process under the same culturing conditions by simply setting the culturing conditions of the first subculturing process through the condition setting unit prior to performing the first subculturing process.

In the aspect described above, the feature value computing unit may fit a preliminarily set growth curve to the data acquired in the first subculturing process, and may output coefficients obtained as a result as the growth feature values.

In this manner, the growth characteristics of the second subculturing process can be easily estimated on the basis of the coefficients obtained by fitting the growth curve to the data acquired in the first subculturing process, and the correlation of the growth characteristics between the two subculturing processes.

In the aspect described above, three or more subculturing processes may be included in the culture period, and the first subculturing process may be the second or later subculturing process from start of the culture period.

Since the state of the cells is unstable in the subculturing process performed first after the start of the culture period, it is difficult to obtain a correlation of the growth curves between that subculturing process and the next subculturing process. However, in the aforementioned manner, by using more strongly correlated growth characteristics of the first subculturing process performed second or later, the growth characteristics of the second subculturing process one process after the first subculturing process can be highly accurately estimated.

In the aspect described above, a freezing period for freezing the cells may be included between the first subculturing process and the second subculturing process.

In this manner, since growth of the cells stops during the freezing period, the starting time of the second subculturing process can be changed by adjusting the length of the freezing period, and the schedule for obtaining a final cell yield can be adjusted.

In the aspect described above, the information computing unit may compute growth characteristics of the cells in the second subculturing process or growth feature values indicating the features of the growth characteristics.

In this manner, on the basis of the growth characteristics or growth feature values computed by the information computing unit, the starting time or ending time of the second subculturing process can be estimated.

In the aspect described above, the condition setting unit may set the culturing conditions including an ending time of the second subculturing process; and, on the basis of the culturing conditions set by the condition setting unit, the information computing unit may compute, as the characteristics-related information, a starting time of the second subculturing process in order to end the second subculturing process at the ending time.

In this manner, when the culturing conditions including the ending time of the second subculturing process are set in the condition setting unit, the starting time of the second subculturing process is computed by the information computing unit. Thus, by starting the second subculturing process at the computed starting time, the second subculturing process can be ended at the target ending time. In other words, the second subculturing process can be started so that the subculture can end at the predesignated ending time of the culture period.

In the aspect described above, the condition setting unit may set, as the culturing conditions, a starting time and an ending time of the second subculturing process; and, on the basis of the starting time and the ending time set by the condition setting unit, the information computing unit may compute, as the characteristics-related information, other culturing conditions of the second subculturing process in order to end the second subculturing process at the ending time.

In this manner, when the starting time and ending time of the second subculturing process are set in the condition setting unit, other culturing conditions needed to obtain the target cell yield at the set ending time by starting the subculture at the set starting time are computed. Thus, by performing the second subculturing process under the computed culturing conditions, the target cell yield can be obtained at the ending time.

Another aspect of the present invention provides a culture information processing device including: an input device through which data acquired in a first subculturing process selected from among a plurality of subculturing processes included in a culture period of cells and culturing conditions of a second subculturing process one process after the first subculturing process are input; a storage that stores the data and the culturing conditions input through the input device; and a processor that computes, on the basis of the data and the culturing conditions stored in the storage, characteristics-related information related to growth characteristics of the second subculturing process. The processor computes growth feature values indicating the features of growth characteristics of the cells in the first subculturing process from the data stored in the storage, and computes the characteristics-related information on the basis of the computed growth feature values and the culturing conditions stored in the storage.

Yet another aspect of the present invention provides a culture information processing device including: a storage that stores data acquired in a first subculturing process selected from among a plurality of subculturing processes included in a culture period of cells and culturing conditions of a second subculturing process one process after the first subculturing process; and a processor that computes, on the basis of the data and the culturing conditions stored in the storage, characteristics-related information related to growth characteristics of the second subculturing process. The processor computes growth feature values indicating the features of growth characteristics of the cells in the first subculturing process from the data stored in the storage, and computes the characteristics-related information on the basis of the computed growth feature values and the culturing conditions stored in the storage.

Still another aspect of the present invention provides a culture information processing device, in which growth feature values that indicate features of growth characteristics of cells in a first subculturing process selected from among a plurality of subculturing processes included in a culture period of the cells and that are computed on the basis of data acquired in the first subculturing process, and culturing conditions of a second subculturing process one process after the first subculturing process are input, and, on the basis of the input growth feature values and culturing conditions, characteristics-related information related to growth characteristics of the second subculturing process is computed.

REFERENCE SIGNS LIST 1 culture information processing device
2 cell counter (input device)
3 input device (condition setting unit)
4 storage
5 processor
7 feature value computing unit
8 information computing unit
14 cloud server (culture information processing device)
A, B, C culturing conditions

The invention claimed is:
1. A culture information processing device comprising:
   a feature value computing unit that computes growth feature values indicating features of growth characteristics of cells from data acquired in a particular first subculturing process selected from among a plurality of subculturing processes included in a culture period of the cells;
   a condition setting unit that sets culturing conditions of a second subculturing process one process after the first subculturing process; and
   an information computing unit that computes, on the basis of the growth feature values computed by the feature value computing unit and the culturing conditions set by the condition setting unit, characteristics-related information related to growth characteristics in the second subculturing process.
2. The culture information processing device according to claim 1, wherein the condition setting unit sets culturing conditions of the first subculturing process, and sets, for the second subculturing process, culturing conditions other than when to culture to be identical to the culturing conditions of the first subculturing process.
3. The culture information processing device according to claim 1, wherein the feature value computing unit fits a preliminarily set growth curve to the data acquired in the first subculturing process, and outputs coefficients obtained as a result as the growth feature values.
4. The culture information processing device according to claim 1, wherein three or more subculturing processes are included in the culture period, and
   the first subculturing process is the second or later subculturing process from start of the culture period.

5. The culture information processing device according to claim 1, wherein a freezing period for freezing the cells is included between the first subculturing process and the second subculturing process.
6. The culture information processing device according to claim 1, wherein the information computing unit computes growth characteristics of the cells in the second subculturing process or growth feature values indicating features of the growth characteristics.
7. The culture information processing device according to claim 1, wherein the condition setting unit sets the culturing conditions including an ending time of the second subculturing process; and
   on the basis of the culturing conditions set by the condition setting unit, the information computing unit computes, as the characteristics-related information, a starting time of the second subculturing process in order to end the second subculturing process at the ending time.
8. The culture information processing device according to claim 1, wherein the condition setting unit sets, as the culturing conditions, a starting time and an ending time of the second subculturing process; and
   on the basis of the starting time and the ending time set by the condition setting unit, the information computing unit computes, as the characteristics-related information, other culturing conditions of the second subculturing process in order to end the second subculturing process at the ending time.
9. A culture information processing device comprising:
   an input device through which data acquired in a first subculturing process selected from among a plurality of subculturing processes included in a culture period of cells and culturing conditions of a second subculturing process one process after the first subculturing process are input;
   a storage that stores the data and the culturing conditions input through the input device; and
   a processor that computes, on the basis of the data and the culturing conditions stored in the storage, characteristics-related information related to growth characteristics of the second subculturing process,
   wherein the processor computes growth feature values indicating features of growth characteristics of the cells in the first subculturing process from the data stored in the storage, and computes the characteristics-related information on the basis of the computed growth feature values and the culturing conditions stored in the storage.
10. A culture information processing device comprising:
   a storage that stores data acquired in a first subculturing process selected from among a plurality of subculturing processes included in a culture period of cells and culturing conditions of a second subculturing process one process after the first subculturing process; and
   a processor that computes, on the basis of the data and the culturing conditions stored in the storage, characteristics-related information related to growth characteristics of the second subculturing process,
   wherein the processor computes growth feature values indicating features of growth characteristics of the cells in the first subculturing process from the data stored in the storage, and computes the characteristics-related information on the basis of the computed growth feature values and the culturing conditions stored in the storage.
11. A culture information processing device, wherein growth feature values that indicate features of growth characteristics of cells in a first subculturing process selected from among a plurality of subculturing processes included in a culture period of the cells and that are computed on the basis of data acquired in the first subculturing process, and culturing conditions of a second subculturing process one process after the first subculturing process are input, and on the basis of the input growth feature values and culturing conditions, characteristics-related information related to growth characteristics of the second subculturing process is computed.

* * * * *